United States Patent [19]

Stoll et al.

[11] Patent Number: 5,342,869
[45] Date of Patent: Aug. 30, 1994

[54] STABILIZED POLYMERIC COMPOSITIONS

[75] Inventors: Klaus Stoll, Rümmingen, Fed. Rep. of Germany; Rainer Wolf, Allschwil, Switzerland

[73] Assignee: Sandoz Ltd., Basel, Switzerland

[21] Appl. No.: 909,547

[22] Filed: Jul. 6, 1992

[30] Foreign Application Priority Data

Jul. 3, 1991 [GB] United Kingdom ............... 9114430

[51] Int. Cl.$^5$ ................. C08K 5/5393; C07F 9/48
[52] U.S. Cl. ................. 524/125; 524/117; 524/119; 558/77; 558/84; 558/162
[58] Field of Search ............ 558/156, 162, 215; 524/125, 132

[56] References Cited

U.S. PATENT DOCUMENTS

| | | | |
|---|---|---|---|
| 3,875,264 | 4/1975 | Hofer et al. | 558/156 |
| 3,903,208 | 9/1975 | Hofer et al. | 558/156 X |
| 4,261,880 | 4/1981 | Fujii et al. | 260/45.8 |
| 4,444,930 | 4/1984 | Guerin et al. | 524/125 |
| 4,999,393 | 3/1991 | Haruna et al. | 558/83 X |
| 5,109,043 | 4/1992 | Böhshar et al. | 558/134 X |

FOREIGN PATENT DOCUMENTS 62-4418 11/1977 Japan .

OTHER PUBLICATIONS

*Registry Handbook* Number Section; 1988 Supplement; American Chemical Society: 1988; No. 112949-97-0.

*Primary Examiner*—Robert W. Ramsuer
*Assistant Examiner*—Michael G. Ambrose
*Attorney, Agent, or Firm*—Robert S. Honor; Richard E. Vila; Andrew N. Parfomak

[57] ABSTRACT

A composition, having good weatherability properties, comprising
a) one or more compounds of formula I

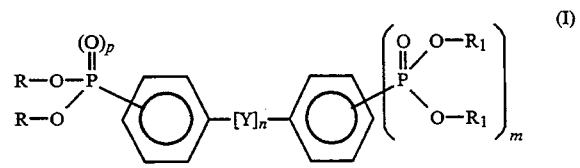

in which
m is 1;
n is 0 or 1;
p is 0;
each R or R$^1$ independently, is a group derived from an aliphatic, alicyclic or aromatic alcohol containing one or two OH groups; whereby the two —OH groups are not positioned to be able to form a P-containing ring;
or both groups R form a group derived from an aliphatic, alicyclic or aromatic alcohol containing two OH groups in such a position that they can form a cyclic group with a single phosphorus atom;
Y is —O—, —S—, —CH(R$_5$)— or —C$_6$H$_4$—;
where R$_5$ is hydrogen or C$_{1-8}$alkyl or COOR$_6$ and R$_6$ is C$_{1-8}$alkyl; and
b) a polymeric material.

10 Claims, No Drawings

STABILIZED POLYMERIC COMPOSITIONS

The invention relates to new additive compositions for polymeric materials, which surprisingly improve the polymer degradation during weathering.

According to the invention there is provided a composition, having good weatherability properties, comprising a) one or more compounds of formula I (hereinafter defined as component a)

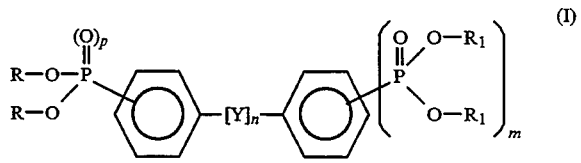

in which
m is 0 or 1;
n is 0 or 1;
p is 0 or 1;
each R, independently, is a group derived from an aliphatic, alicyclic or aromatic alcohol containing one or two OH groups; whereby the two —OH groups are not positioned to be able to form a P-containing ring; (hereinafter defined as the monovalent significances of R);
or both groups R form a group derived from an aliphatic, alicyclic or aromatic alcohol containing two OH groups in such a position that they can form a cyclic group with a single phosphorus atom (hereinafter defined as the divalent significances of R);
each $R_1$ independently is a group derived from an aliphatic, alicyclic or aromatic alcohol containing one or two OH groups; whereby the two —OH groups are not positioned to be able to form a P-containing ring (hereinafter defined as the monovalent significances of $R_1$);
or both groups $R_1$ form a group derived from an aliphatic, alicyclic or aromatic alcohol containing two OH groups in such a position that they can form a cyclic group with a single phosphorus atom (hereinafter defined as the divalent significances of $R_1$);
Y is —O—, —S—, —CH($R_5$)— or —$C_6H_4$—;
where $R_5$ is hydrogen or $C_{1-8}$alkyl or COO$R_6$ and $R_6$ is $C_{1-8}$alkyl; and b) a polymeric material (hereinafter defined as component b).

The foregoing definitions of R and $R_1$ are intended to include each R and $R_1$, independently, being an aliphatic, alicyclic or aromatic group containing up to one OH group, provided that said OH group and the —O— attached to the same R or $R_1$ are not positioned so as to be able to form, together with the same phosphorus atom, an —O—P—O— group (monovalent significances of R and $R_1$) and both groups R together and/or, separately, both groups $R_1$ together forming an aliphatic, alicyclic or aromatic group to which the two —O— groups are attached in such positions that they can form, together with the same phosphorus atom, an —O—P—O— group (divalent significances of R and $R_1$).

Preferably, in a composition according to the invention, the amount of component a present is 0.001 to 2% and the amount of component b present is 99.999–98% based on the combined weight of component a and component b.

Compositions according to the invention may additionally contain one or more of the following components:

c) a compound of formula II (herein after defined as component c)

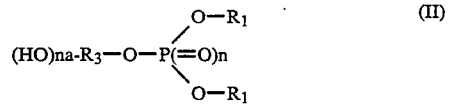

in which
n is 0 or 1;
na is 0 or 1.
$R_3$ has a monovalent significance of R; and d) a compound of formula IV or V (hereinafter defined as component d)

in which, in formula IV, $R_7$ is a monovalent significance of R and $R_8$ is a divalent significance of R; and e) a phosphonite of formula X (hereinafter defined as component e)

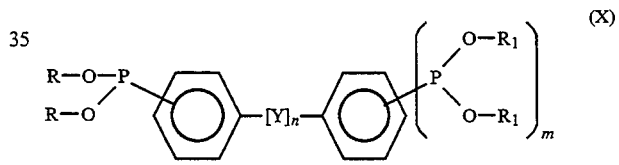

in which R, $R_1$, Y and n are as defined above.

Preferably the combined amount of components a), c), d) and e) based on 100 parts of component b) is 0.001 to 2 parts.

Preferably the ratio of the amounts of components a) c) d) and e) are as follows:
a) 10 to 98 parts of component a);
b) 2 to 50 parts of component e);
c) 0 to 40 parts of the phosphite of formula II and the phosphate of formula II (together component c); preferably in an approximate ratio of 5:1 to 1:5; and
d) 0.1 to 5 parts of component d), preferably based on 100 total parts by weight of components a), c), d) and e).

A most preferred composition according to the invention comprises
a) 45 to 95 parts of component a) as defined above;
b) 4.5 to 35 parts of component e) as defined above;
c) 0 to 20 parts of component c) as defined above; and
d) 0.5 to 2 parts of component d) as defined above;
preferably based on 100 parts by weight of components a, c, d and e.

Preferably R is R' where R' is an alkyl, aralkyl, aryl, alkaryl aminoalkyl or aminoaryl group (hereinafter referred to as the monovalent significances of R'); or both groups R' together form a group of formula α

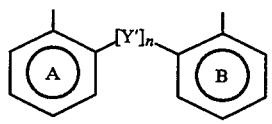
(a)

where phenyl groups A and B may be further substituted and Y' is —O—, —S— or —CH(R$_5$)— where R$_5$ is hydrogen or C$_{1-8}$alkyl or COOR$_6$ where R$_6$ is C$_{1-8}$alkyl (hereinafter defined as the divalent significances of R').

More preferably R is R" where R" is selected from C$_{1-22}$alkyl; phenyl, unsubstituted or substituted by 1 to 3 groups selected from C$_{1-22}$alkyl, C$_{1-22}$alkoxy, —CH$_2$—C$_6$H$_5$; —C$_6$H$_5$, 2,2,6,6-tetramethylpiperidinyl-4-, —C(CH$_3$)$_2$—C$_6$H$_5$, —OH (maximum of one ), -(C$_{1-6}$alkyl)phenyl, —CO$_2$-C$_{1-22}$alkyl, —CH$_2$CH$_2$—COOR$_{15}$, CN or —CH$_2$—S-C$_{1-22}$alkyl; or R" is a group of any one of formulae i to vii

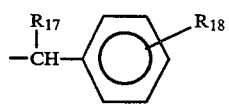
(i)

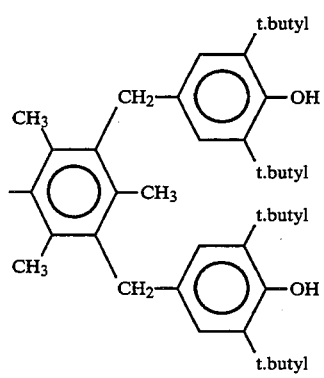
(ii)

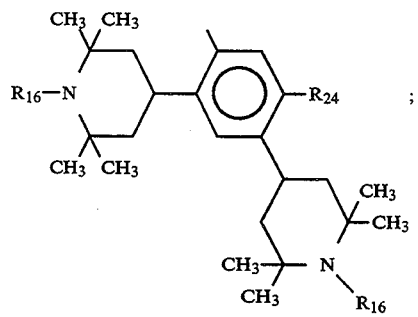
(iii)

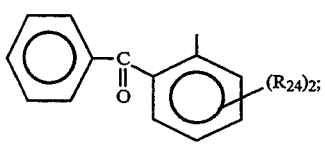
(iv)

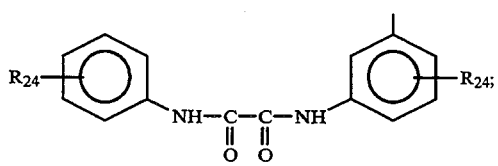
(v)

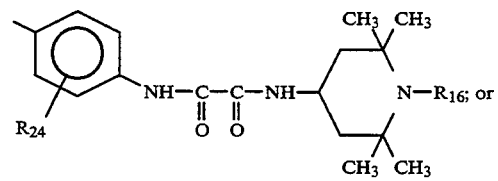
(vi)

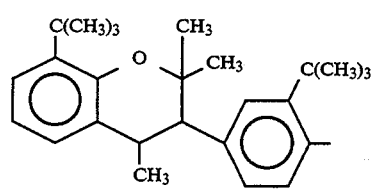
(vii)

or both groups R" together form a group of formula viii

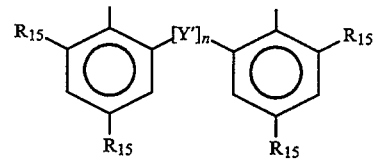
(viii)

where R$_{15}$ is hydrogen or C$_{1-22}$alkyl;
Y' is O, —S— or —CH(R$_5$)—;
R$_{16}$ is hydrogen, C$_{1-8}$alkyl or —COC$_{1-8}$alkyl;
R$_{17}$ is hydrogen or C$_{1-22}$alkyl; and
R$_{18}$ is hydrogen, C$_{1-22}$alkyl, C$_{1-22}$alkoxy, —CH$_2$—C$_6$H$_5$, —C(CH$_3$)$_2$—C$_6$H$_5$, —C$_6$H$_5$, —OH, —CH$_2$CH$_2$COOR$_{15}$, -(C$_{1-6}$alkyl)phenyl, —CO$_2$-C$_{1-22}$alkyl, —CN, —CH$_2$CH$_2$—COOR$_{15}$, —CH$_2$—S-C$_{1-22}$alkyl or 2,2,6,6-tetramethylpiperidinyl-4-; and
R$_{24}$ is hydrogen, C$_{1-22}$alkyl, OH or C$_{1-22}$alkoxy.

Most preferably R is R'" where R'" is selected from a group of any one of formulae a) to g)

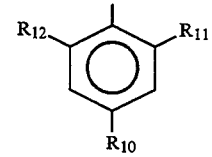
(a)

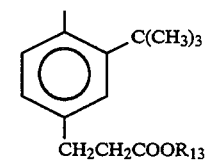
(b)

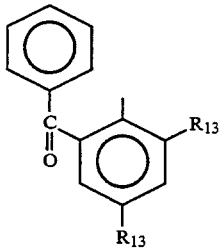
(c)

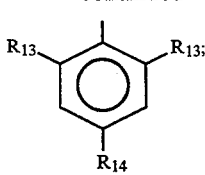
(d)

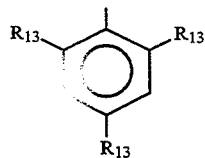
(e)

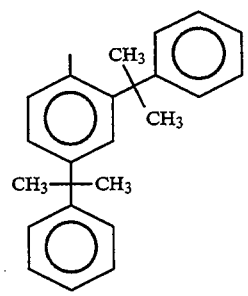
(f)

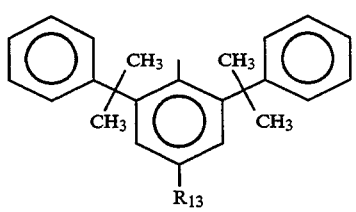
(g)

in which

R$_{10}$ is hydrogen, C$_{1-8}$alkyl, C$_{1-8}$alkoxy or (C$_{1-8}$alkyl)-phenyl;

R$_{11}$ and R$_{12}$ independently are selected from hydrogen, C$_{1-22}$alkyl, C$_{1-8}$alkyl)phenyl and phenyl;

R$_{13}$ is selected from hydrogen and C$_{1-8}$alkyl;

R$_{14}$ is —CN or —CO$_2$R$_{13}$; and

R$_{15}$ is hydrogen or C$_{1-8}$alkyl.

Preferred groups of (a) are selected from 2-tert.butyl-phenyl; 2-phenylphenyl; 2-(1,1-dimethyl propyl)phenyl; 2-cyclohexylphenyl; 2-tert.butyl-4-methyl phenyl; 2,4-di-tert.amyl phenyl; 2,4-di-tert.butyl phenyl; 2,4-diphenylphenyl; 2,4-di-tert.octyl phenyl; 2-tert.butyl-4-phenyl-phenyl; 2,4-bis(1,1-dimethylpropyl)phenyl; 2-(1-phenyl-1-methylethyl)phenyl; 2,4-bis(1-phenyl-1-methylethyl)phenyl; and 2,4-ditert.butyl-6-methylphenyl.

Preferably R$_1$ is R$_1'$ where R$_1'$ has a significance of R' independently of R'. More preferably R$_1$ is R$_1''$ where R$_1''$ has a significance of R'' independently of R''. Most preferably R$_1$ is R$_1'''$ where R$_1'''$ has a significance of R''', independent of R'''.

Preferably, R$_3$ and R$_7$ have, independently, a monovalent significance of R', more preferably of R'', most preferably of R'''.

Preferably, R$_8$, independently, has a divalent significance of R', more preferably of R''.

In formulae I and X, preferably m is 1.

Preferably component a) contains a) a diphosphonate of formula I defined above (hereinafter defined as component I);

b) a monophosphonate of formula I defined above (hereinafter defined as component II); and c) a phosphonate-phosphonite of formula I in which m=1 and p=0 (hereinafter defined as component III.

Preferably component a) contains

10–70 parts of component I;

2–30 parts of component II; and

5–40 parts of component III.

Preferably the compound of formula I is a diphosphonate, more preferably it is tetrakis (2,4-di-tert.-butyl phenyl)-biphenylene diphosphonate.

Preferably component e) is present in a composition according to the invention and the compound (or compounds if more than one is present) of formula X correspond to the phosphonate (or phosphonates where more than one is present) of formula I. Preferably the components a) and e) are present in a ratio of 19:1 to 9:7.

For the avoidance of doubt, where a symbol appears more than once in a formula or once in two different formulae of a stabilising composition according to the invention, its significances are independent unless indicated to the contrary. However, where in a stabilising composition, a symbol appears in a formula, the significances of the symbol are preferably the same.

In a composition according to the invention preferably R$_1$ has the same significance as R.

Compounds of formula I can be prepared by reacting a) 2 moles of a compound of formula IX

where R$_{30}$ has a monovalent significance of R; and 2 moles of a compound of formula XI

where R$_{31}$ has a monovalent significance of R$_1$; with 1 mole of a compound of formula XIV

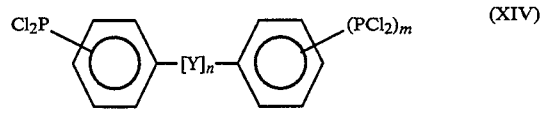

where Y and n are as defined above; or b) 1 mole of a compound of formula XII

where R$_{32}$ has a divalent significance of R$_1$ defined above; and 2 moles of a compound of formula IX defined above;

with 1 mole of a compound of formula XIV as defined above; or c) 1 mole of a compound of formula XII defined above; and 1 mole of a compound of formula XIII

where R$_{33}$ has a divalent significance of R; at an elevated temperature (preferably 40°–140° C.); followed by oxidising the resulting product to form a compound of formula I.

Further, according to the invention, there is provided a compound of formula XV

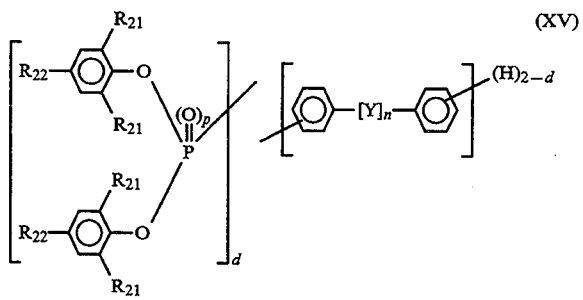

where n is 0 or 1; (preferably n=0)
d is 1 or 2;
p is 0 or 1;
each $R_{21}$ independently is hydrogen, $C_{1-4}$alkyl (preferably t.butyl or methyl) or —$C(CH_3)_2$—$C_6H_5$; and
each $R_{22}$ independently has a significance of $R_{21}$ independent of $R_{21}$; and Y is as defined above.

Further, according to the invention there is provided a compound of the formula XVI

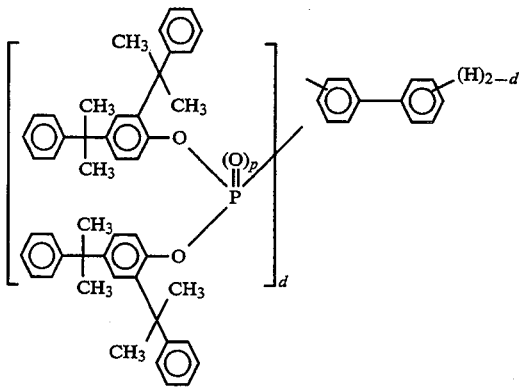

where d is 1 or 2 and p is 0 or 1. Preferably d is 2.

Preferably the amount of component a) (and when present any one of components c), d) and e)) in a polymeric composition are from 0.001 to 1%; more preferably 0.05 to 0.3% by weight based on the amount of component b).

Preferably in a composition according to the invention components a) to e) are all present.

It has been found that a combination of a) and c) and optionally e) in a composition according to the invention produces a synergistic effect on the stability of a polymeric composition to which it is applied.

It has been found that properties such as stability to light, oxygen, hydrolysis, high temperature, humidity, ozone and smog are improved.

Component b) is preferably an α-polyolefin prepared using catalysts of the first to fifth (I to V) Generation hereinafter defined.

Further polymeric materials that can be stabilised by a composition according to the invention include homopolymers, copolymers and polymer blends of:

Cellulose acetate; Cellulose acetatobutyrate; Cellulose acetopropionate; Cresol-formaldehyde resin; Carboxymethylcellulose; Cellulose nitrate; Cellulose propionate; Casein plastics; Casein-formaldehyde; Cellulose triacetate; Ethyl cellulose; Epoxy resins; Methyl cellulose; Melamine-formaldehyde resins; Polyamide; Polyamideimide; Polyacrylonitrile; Polybutene-1; Polybutylacrylate; Polybutyleneterephthalate; Polycarbonate; Poly(chloro trifluoroethylene); Poly(diallylphthalate); Polyethylene; chlorinated Polyethylene; Poly(etherketone); Polyetherimide; Polyethyleneoxide; Polyethersulphone; Polyethyleneterephthalate; Polytetrafluoroethylene; Phenol-formaldehyde resins; Polyimide; Polyisobutylene; Polyisocyanurate; Polymethacrylimide; Polymethylmethacrylate; Poly(4-methylpenten-1); Poly(α-methyl styrene); Polyoxymethylene; Polyformaldehyde; Polyacetal; Polypropylene; Polyphenylene ether; Polyphenylenesulphide; Polyphenylenesulphone; Polystyrene; Polysulphone; Polyurethane; Polyvinyl acetate; Polyvinyl alcohol; Polyvinylbutyral; chlorinated Polyvinyl chloride; Polyvinylidene chloride; Polyvinylidene fluoride; Polyvinylfluoride; Polyvinylformaldehyde; Polyvinylformaldehyde; Polyvinylcarbazol; Polyvinylpyrrolidone; Silicon polymers; saturated polyester; urea-formaldehyde resins; unsaturated polyester; polyacrylate; polymethacrylate; polyacrylamide; maleinate resins; phenolic resins; aniline resins; furane resins; carbamide resins; epoxide resins and silicon resins.

Examples of suitable copolymers include:
Acrylonitrile/butadiene/acrylate; Acrylonitrile/butadiene/styrene; Acrylonitrile/methylmethacrylate; Acrylonitrile/styrene/acrylic ester; Acrylonitrile/ethylene-propylenediene/styrene; Acrylonitrile/ chlorinated polyethylene/styrene; Ethylene/ethylacrylate; Ethylene methacrylic acid ester; Ethylene/propylene; Ethylene/propylene-diene; Ethylene/vinyl acetate; Ethylene/vinyl alcohol; Ethylene/tetrafluoroethylene; Tetrafluoroethylene/hexafluoropropylene; Methacrylate/butadiene/styrene; Melamine/phenol-formaldehyde; Polyester blockamide; Perfluoro-alkoxy-alkane; Styrene/acrylonitrile; Styrene/butadiene; Styrene/maleic acid anhydride; Styrene/α-methylstyrene; Vinylchloride/ethylene; Vinylchloride/ethylene/methacrylate; Vinylchloride/ethylene/vinyl acetate; Vinylchloride/methylmethacrylate; Vinylchloride/octylacrylate; Vinylchloride/vinyl acetate; and Vinylchloride/vinylidene chloride.

Preferred polymeric materials to be stabilised are polyolefins such as polypropylene, polyethylene (e.g. high density polyethylene, low density polyethylene, linear low density polyethylene or medium density polyethylene), polybutylene, poly-4-methylpentene and copolymers thereof.

Further additives that can be added to a stabilising or a polymeric composition according to the invention include antioxidants, such as sterically hindered phenols, secondary aromatic amines or thioethers, such as described in "Kunststoff-Additive"-Gächter/Müller, Ed. 3, 1990 p.42–50, the contents of which are incorporated herein by reference; U.V. stabilisers such as sterically hindered amines (for example N-unsubstituted, N-alkyl or N-acyl substituted 2,2,6,6-tetra-methylpiperidine compounds) [also known as hindered amine light stabilisers-HALS] and U.V. absorbers (e.g. 2-(2'-hydroxyphenyl)-benztriazoles, 2-hydroxybenzophenones, 1,3-bis-(2'-hydroxybenzoyl-) benzene salicylates, cinnamates and oxalic acid diamides;), U.V. quenchers such as benzoates and substituted benzoates, antistatic agents, flameproofing agents, softeners, nucleating agents, metal deactivators, biocides, impact modifiers, fillers, pigments and fungicides.

Stabilising compositions according to the invention may be added to the polymeric material before, during or after the polymerization step and may be added in solid or molten form, in solution preferably as a liquid concentrate containing from 10 to 80% by weight of the composition and 90 to 20% by weight of solvent or as a solid masterbatch composition containing 10 to 80% (more preferably 40 to 70%) by weight of the composition and 90 to 20% (more preferably 60 to 30%) by weight of a solid polymeric material which is identical with or compatible with the material to be stabilized.

The compositions according to the invention may be incorporated by known methods into the polymeric material to be stabilized. Of particular importance is blending of the compounds with thermoplastic polymers in the melt, for example in a melt blender or during the formation of shaped articles, including foils, tubes, fibres and foams by extrusion, injection moulding, blow moulding, spinning or wire coating. The compositions according to the invention are particularly useful for polypropylene articles, manufactured by injection moulding.

Further, in this specification, where a range is given, the figures defining the range are included therein. Any group capable of being linear or branched is linear or branched unless indicated to the contrary.

For the avoidance of doubt, in this specification t-butyl means tertiary butyl, (—C(CH₃)₃).

Further according to the invention there is provided a compound of formula I in which m is 1 and p is 0.

Preferred polyolefins are α-polyolefins prepared by using catalysts of the third to the fifth (III to V) Generations in a polymerisation process, in which a catalyst removal step is not necessary, indeed the catalyst is preferably not removed.

What we mean by Generation I catalysts are the classic Ziegler-Natta systems, based on titanium halide catalysts and an organo aluminium compound or an organo aluminium halide.

What we mean by Generation II catalysts are Generation I catalysts supported on an organo magnesium compound or based on an organo chromium compound supported on SiO₂.

What we mean by a Generation III catalyst is a Ziegler type complex catalyst supported on a halogen containing magnesium compound.

What we mean by a Generation IV catalyst is a Generation III catalyst with additional electron donors, e.g. trisalkoxy silanes.

What we mean by Generation V catalysts are bis indenyl organo titanium compounds supported on alumoxane or biscyclopentadienyl titanium halides activated by aluminium alkyl compound or any similar systems, combining high catalyst activity and leading to high stereoregularity of the formed polymerisation product.

These generations of catalysts are described in the Twelfth Annual International Conference on Advances in the Stabilisation and Controlled Degradation of Polymers held in Luzern 21-23 May 1990 in an article on pages 181 to 196 inclusive by Rolf Mülhaupt entitled "New Trends in Polyolefin Catalysts and Influence on Polymer Stability." The contents of this article is incorporated herein by reference and especially Table I on page 184 describing the Generation of Catalysts:

TABLE 1

Polyolefin Catalyst Evolution

| | Generation Example | Cat. Act. (gPP/gTi hatm) | % Act. Ti | Stereoreg. (% hept. ins.) | Process Technology |
|---|---|---|---|---|---|
| I. | TiCl₄/AlR₃ | 40 | 0.01 | 45% | removal of cat. residues and atactic PP |
| | TiCl₃/AlEt₂Cl | 30 | 0.1 | 92% | removal of catalyst residues |
| II | Mg(OEt₂)/TiCl₄/AlR₃ | 40000 | | 50% | no removal of cat. residues (mainly HDPE/LLDPE) |
| | SiO₂/Cp₂Cr | 40000 | HDPE | | |
| III | Mod. TiCl₃cat. | 5000 | 1 | 95% | no purification |
| | MgCl₂/TiCl₄/AlE₃ -ester donor | 40000 | 10 | 92% | |
| IV | MgCl₂/TiCl₄/AlR₃ -silane donor | 40000 | 18 | 99% | no purification no extrusion |
| V | Bis-idenyl-TiR₂ on (AlCH₃O)₂ | 40000 | 100 | 99% | novel PPs, narrow MWD | in which R is an organo group; HDPE is high density polyethylene, LLDPE is linear low density polyethylene, Cp is cyclopentadienyl, Et is ethyl, PP is polypropylene, MWD is molecular weight distribution and x is an integer above 2.

Further according to the invention there is provided a composition having improved weatherability properties and good stability comprising
a) tetrakis (2,4-di-tert-butyl phenyl)-biphenylene diphosphonite and/or a phosphite of Formula II and
b) a polyolefin resin which has been produced in the presence of a Generation V catalyst, preferably bis indenyl organo titanium compounds supported on alumoxane or biscyclpentadienyl titanium halide activated by aluminum alkyl compound as hereinabove defined.

Preferably such a composition also includes
c) tetrakis (2,4-di-tert-butyl-phenyl)-biphenylene phosphonite-phosphonate and tetrakis(2,4-di-tert-butyl-phenyl)-biphenylene diphosphonate.

Further according to the invention there is provided a composition having improved weatherability properties and good stability comprising
a) tetrakis (2,4-di-tert.-butyl phenyl)-biphenylene diphosphonite and/or a phosphite of Formula II and
b) a polyolefin resin which has been produced in the presence of a Generation IV catalyst, preferably a Ziegler type complex catalyst supported on a halogen containing magnesium compound with one or more additional electron donors, preferably a trisalkoxy silane.

Preferably such a composition also includes
c) tetrakis (2,4-di-tert-butyl-phenyl)-biphenylene phosphonite-phosphonate and tetrakis(2,4-di-tert-butyl-phenyl)-biphenylene diphosphonate.

Phosphonites (especially tetrakis (2,4-di-tert.-butyl phenyl)-biphenylene diphosphonite) will be useful as processing stabilisers and for improving weatherability of any α-polyolefins manufactured by a catalyst of still more enhanced acitivity and/or resulting in a polymer of stereoregularity due to their known properties during polymer processing.

Phosphonates (especially tetrakis (2,4-di-tert.-butyl phenyl)-biphenylene diphosphonates) and/or phosphonates-phosphonites (e.g. tetrakis(2,4-tert-butyl-phenyl)biphenylene-4-phosphonite-4'-phosphonate) and/or mixtures thereof which are applied in α-polyolefins will be useful to improve weatherability of any α-polyolefin made by using future generations of polymer processing catalysts.

Mixtures of the diphosphonites and/or diphosphonates and/or phosphonite/phosphonates with the corresponding monophosphonites and/or monophosphonates respectively will also be suitable for stabilising α-polyolefins made by using future generations of processing catalysts and/or for improving weatherability of the resultant polymers.

The invention will now be illustrated by the following Example in which all parts and percentages are by weight and all temperatures are in °C. unless indicated to the contrary.

EXAMPLE

Polypropylene compositions are prepared as follows:

| Component | Parts by weight | | | | | |
|---|---|---|---|---|---|---|
| | A | B | C | D | E | F |
| Polypropylene | 100 | 100 | 100 | 100 | 100 | 100 |
| Antioxidant | 0.1 | 0.1 | 0.1 | 0.1 | 0.1 | 0.1 |
| Processing Stabiliser | — | — | 0.1 | 0.1 | — | 0.1 |
| Compound of formula Ia | — | 0.1 | — | 0.1 | — | — |
| Compound of formula Ib | — | — | — | — | 0.1 | 0.1 |

Polypropylene used is Hostalen PPN 0160-F

The antioxidant used is tetrakis[methylene-3(3',5'-di-tert.butyl-4'-hydroxy-phenyl)propionate]methane commercially available as Irganox 1010;

The compound of formula Ia is tetrakis (2,4-di-tert.-butyl phenyl)-biphenylene diphosphonate The compound of formula Ib is bis(2,4-ditert.butyl-phenyl)biphenylene phosphonate; and The processing stabiliser is tris(2,4 di tert.butyl phenyl)phosphite (commercially available as Irgafos 168).

The polypropylene is processed by Göttfert extruder having a 20 mm screw (compression 1:3, diameter to length [d:1:20) at 250° C. This was worked into plaques as follows:

The resultant polymer is formed into sheets 0.5 mm thick by means of high pressure moulding under the following conditions.

| preheating: | 230° C., low pressure, | 3 minutes |
|---|---|---|
| heating: | 230° C., 80-100 kg/cm², | 2 minutes |
| cooling: | 30° C., 150 kg/cm², | 2 minutes. |

From the resulting sheets, 3 test pieces are cut out for each test run. These test pieces are placed in an Atlas Weatherometer (WOM Ci65 using a Xenon high pressure burner and treated under the conditions of rainfall of 18 min. per 2 hours to determine the time required for cracks to appear on the test pieces.

What is claimed is:

1. A polymeric material composition comprising:
   a diphosphonate of formula I in which $m=1$ and $p=1$;
   a monophosphonate of formula I in which $m=0$ and $p=1$; and
   a phosphonate-phosphonite of formula I in which $m=1$ and $p=0$ in which formula I has the structure:

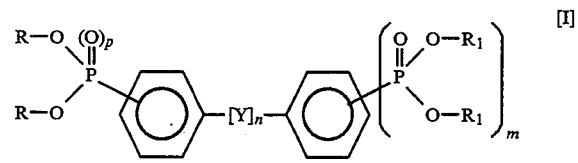

in which
   each R, independently, is a monovalent significance of R, a group derived from an aliphatic, alicyclic or aromatic alcohol containing one or two —OH groups; whereby the two —OH groups are not positioned to be able to form a P-containing ring;
   or a divalent significance of R, where both groups R form a group derived from an alphatic, alicyclic or aromatic alcohol containing two OH groups in such a position that they can form a cyclic group with a single phosphorus atom;
   each $R_1$ independently, is a monovalent significance of $R_1$, a group derived from an aliphatic, alicyclic or aromatic alcohol containing one or two OH groups; whereby the two —OH groups are not positioned to be able to form a P-containing ring;
   or a divalent significance of $R_1$, where both groups $R_1$ form a group derived from an aliphatic, alicyclic or aromaic alcohol containing two OH groups in such a position that they can form a cyclic group with a single phosphorous atom;
   n is 0 or 1;
   Y is —O—, —S—, —C($R_5$)— or —$C_6H_4$—;
   where $R_5$ is hydrogen or $C_{1-8}$alkyl or $COOR_6$ and $R_6$ is $C_{1-8}$alkyl.

2. A composition according to claim 1 in which R is R', a monovalent significance of R, where R' is an alkyl, aralkyl, aryl, alkaryl aminoalkyl or aminoaryl group; or R' is a divalent significance of R', a formula α

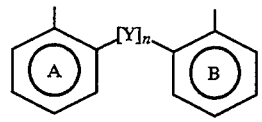

where phenyl groups A and B may be further substituted and Y is —O—, —S—or —CH($R_5$)— where $R_5$ is hydrogen or $C_{1-8}$alkyl or $COOR_6$ where $R_6$ is $C_{1-8}$alkyl.

3. A composition according to claim 2 in which R is R" where R" is selected from $C_{1-22}$alkyl; phenyl, unsubstituted or substituted by 1 to 3 groups selected from $C_{1-22}$alkyl, $C_{1-22}$alkoxy, —$CH_2$—$C_6H_5$; —$C_6H_5$, 2,2,6,6-tetramethyl-piperidin-4-yl, —C($CH_3$)$_2$—$C_6H_5$, —OH, -($C_{1-6}$alkyl)phenyl, —$CO_2$-$C_{1-22}$alkyl, —$CH_2CH_2$—$COOR_{15}$, CN, and —$CH_2$—S-$C_{1-22}$alkyl; or R" is a group of any one of formulae i to vii

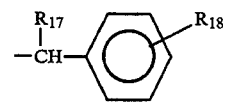

-continued

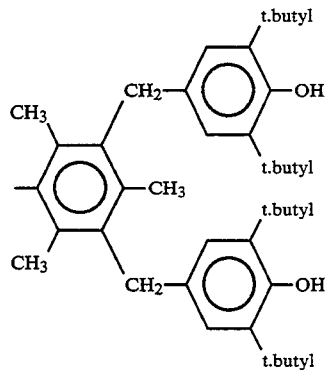

(ii)

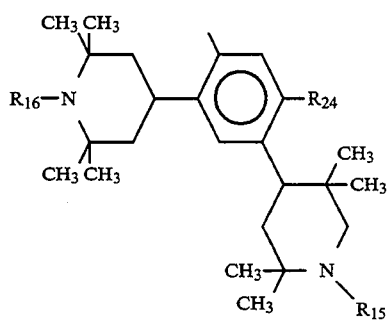

(iii)

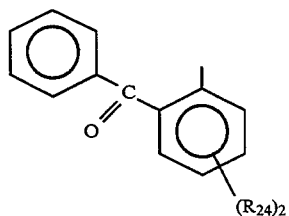

(iv)

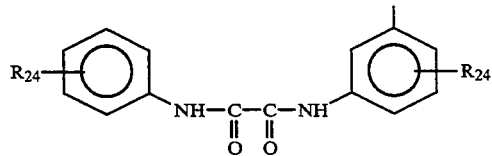

(v)

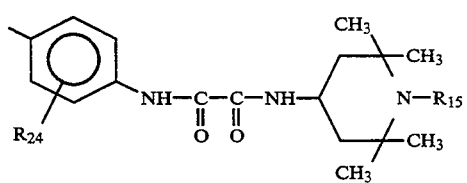

(vi)

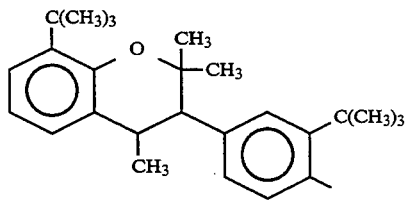

(vii)

or both groups R″ form a group of formula viii

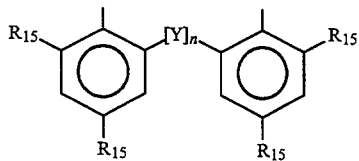

(viii)

where $R_{15}$ is hydrogen or $C_{1-22}$alkyl;

Y is O, —S— or —CH($R_5$)—;

$R_{18}$ is hydrogen, $C_{1-22}$alkyl, $C_{1-22}$alkoxy, —CH$_2$—C$_6$H$_5$, —C(CH$_3$)$_2$—C$_6$H$_5$, —C$_6$H$_5$, —OH, —CH$_2$CH$_2$COOR$_{15}$, -(C$_{1-6}$alkyl)phenyl, —CO$_2$-C$_{1-22}$alkyl, —CN, —CH$_2$CH$_2$—COOR$_{15}$, —CH$_2$—S-C$_{1-22}$alkyl, or 2,2,6,6,-tetramethylpiperiinyl-4-; and $R_{24}$ is hydrogen, $C_{1-22}$alkyl, OH or $C_{1-22}$alkoxy.

4. A composition according to claim 3 in which R is R‴ where R‴ is selected from a group of formulae a) to g)

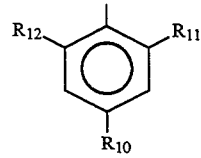

(a)

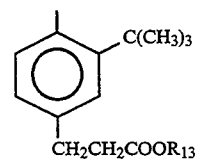

(b)

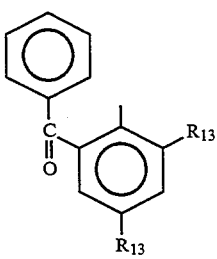

(c)

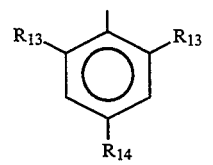

(d)

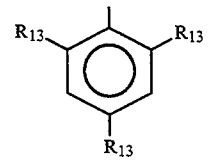

(e)

(f) 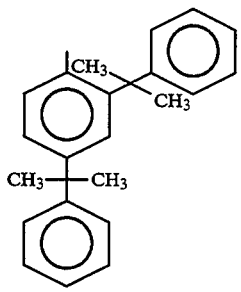

(g) 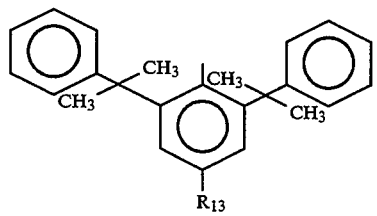

in which $R_{10}$ is hydrogen, $C_{1-8}$alkyl, $C_{1-8}$alkoxy or ($C_{1-8}$alkyl)-phenyl;

$R_{11}$ and $R_{12}$ independently are selected from hydrogen, $C_{1-22}$alkyl, $C_{1-8}$alkyl)phenyl and phenyl;

$R_{13}$ is selected from hydrogen and $C_{1-8}$alkyl;

$R_{14}$ is —CN or —$CO_2R_{13}$.

5. A composition according to claim 1 in which the relative weight ratios per 100 parts of the diphosphonate, monophosphonate and phosphonate-phosphonite are:

10–70 parts of the diphosphonate;

2–30 parts of the monophosphonate; and

5–40 parts of the phosphonate-phosphonite.

6. A composition according to claim 1 in which the total amount of diphosphonate, monophosphonate and phosphonate-phosphonite present is 0.001 to 2% and the amount of the polymeric material present is 99.999–98% based on the combined weight of the diphosphonate, monophosphonate, phosphonate-phosphonite and the polymeric material.

7. A composition according to claim 1 additionally containing one or more of the following optional components:

a compound according to formula II:

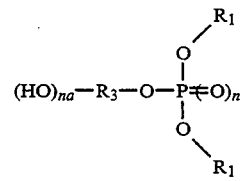

in which n is 0 or 1;

na is 0 or 1;

$R_1$ is as defined in claim 1 and $R_3$ is a monovalent significance of R as defined in claim 1; and;

a compound of formula IV or V $$R_7(OH) \qquad [IV]$$

$$R_8(OH)_2 \qquad [V]$$

wherein in formula IV, $R_7$ is a monovalent signficance of R as defined in claim 1, and in formula V, $R_8$ is a divalent signficance of R as defined in claim 1; and;

a phosphonite of formula X

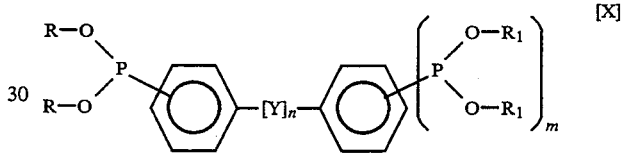

in which R, $R_1$, Y and n are as defined in claim 1.

8. A composition according to claim 7 in which the combined amount of the diphosphonate, monophosphonate and phosphonate-phosphonite, and optionally, the compound of formula II, phenol according to formula IV, phenol according to formula V and phosphonite according to formula X, based on 100 parts of the polymeric material is 0.001 to 2 parts.

9. A composition according to claim 1 in which the polymeric material is an α-polyolefin prepared by using catalysts of the third to the fifth (III to IV) Generations in the polymerization process in which the catalyst is not removed;

Generation III catalysts being Ziegler type complex catalysts supported on a halogen containing magnesium compound;

Generation IV catalysts being Generation III catalysts with additional electron donors; and Generation V catalysts being bis-indenyl organo titanium compounds supported on alumoxane or bis-cyclopentadienyl titanium halides activated by aluminum alkyl compound or any similar systems, combining high catalyst activity and leading to high stereoregularity.

10. A composition according to claim 9 which includes: tetrakis (2,4-di-tert-butyl phenyl)-biphenylene phosphonite-phosphonate, and tetrakis (2,4-di-tert-butyl phenyl)-biphenylene diphosphonate.

* * * * *